United States Patent [19]
Groll et al.

[11] Patent Number: 5,560,742
[45] Date of Patent: Oct. 1, 1996

[54] USE OF PALLADIUM-SILVER ALLOYS FOR THE MANUFACTURE OF DENTURES

[75] Inventors: Werner Groll, Alzenau-Hoerstein; Gernot Schoeck, Bruchkoebel; Doris Hathaway, Hanau; Manfred Stuemke, Pforzheim, all of Germany

[73] Assignee: Degussa AG, Frankfurt am Main, Germany

[21] Appl. No.: 315,915

[22] Filed: Feb. 27, 1989

[30] Foreign Application Priority Data

Feb. 27, 1988 [DE] Germany .................. 38 06 343.3

[51] Int. Cl.⁶ .................................... A61C 13/08
[52] U.S. Cl. .................... 433/206; 433/202.1; 106/35
[58] Field of Search ................. 433/206, 202.1; 106/35

[56] References Cited

U.S. PATENT DOCUMENTS

| | | | |
|---|---|---|---|
| 4,067,853 | 1/1978 | Schmitt et al. | 106/35 |
| 4,198,556 | 1/1989 | Katz | 433/221 |
| 4,321,042 | 3/1982 | Scheicher | 433/202.1 |
| 4,515,634 | 5/1985 | Wu et al. | 433/202.1 |
| 4,943,483 | 7/1990 | Ingersoll et al. | 470/463 |

FOREIGN PATENT DOCUMENTS 8001820  3/1980  Netherlands .

OTHER PUBLICATIONS

*Chemical Abstracts*, 96: 91689c (1982), abstract of Netherland Patent Application 8001820.

*Primary Examiner*—V. Millin
*Attorney, Agent, or Firm*—Beveridge, DeGrandi & Weilacher

[57] ABSTRACT

Gold-free palladium-silver alloys for dentures [dental prostheses] which alloys can be veneered without color changes with dental ceramics and can be easily removed from the mold after the casting contain 45 to 80% by weight palladium, 7 to 50% by weight silver, 0 to 5% by weight gold, 0 to 5% by weight tin, 0 to 5% by weight indium, 0 to 3% by weight zinc, 0 to 2% by weight copper, 0 to 1% by weight ruthenium, iridium and/or rhenium, 0 to 7% by weight gallium, 0 to 5% by weight cobalt and 0 to 3% by weight germanium, whereby of the elements gallium, cobalt and germanium at least two must be present with contents totalling 2 to 9% by weight.

5 Claims, No Drawings

USE OF PALLADIUM-SILVER ALLOYS FOR THE MANUFACTURE OF DENTURES

INTRODUCTION AND BACKGROUND

The present invention relates to the use of palladium-silver alloys for the manufacture of fixed or removable dentures, which can be veneered with dental ceramics.

Fixed or removable dentures are manufactured primarily from corrosion-resistant, biocompatible precious-metal alloys with the so-called precision investment casting, also referred to as the lost-wax process in which the cast object is frequently veneered with dental ceramics in order to achieve an appearance which corresponds to the natural tooth. To be compatible with the dental ceramics the alloys must exhibit special properties, such as coefficient of thermal expansion, melting range or adhesion.

Alloys with a high gold content such as those described, for example, in German patents 11 83 247 and 15 33 233 are especially well-suited for this purpose. However, due to the high and very fluctuating price of gold, more of an effort has been made recently to find more economic alternatives to the alloys with a high gold content. Palladium presents itself from the group of noble metals as an appropriate substitute on account of its relatively economic price, its density, which is considerably less in comparison to that of gold, and its resistance to corrosion in the mouth (oral environment), which is comparable to that of gold.

It is to make a distinction between alloys containing silver and those not containing silver in the previously known palladium-based alloys in the field of dentistry.

Silver-free palladium-based alloys contain copper, tin, indium, cobalt and gallium as main alloying elements. Typical silver-free palladium-based alloys are described for example in German patents 33 16 595; 33 04 183; 33 14 657 or 35 22 523. Compared with alloys with a high gold content, these alloys react more sensitively to manufacturing errors and are difficult to solder. They absorb considerable amounts of carbon in the liquid state, so that they should only be melted in a ceramic crucible. The dark oxides which form during the fixing of the dental ceramics at approximately 980° C. adversely affect the aesthetic appearance of the denture by the formation of dark margins in the edge area of the veneering.

Silver-containing palladium-based alloys fall between the alloys with a high gold content and the silver-free palladium-based alloys as concerns their working behavior. As a result of the silver portion, they are easier to melt and to cast, have a brighter oxide and a good soldering behavior. In addition, they are more economical than the silver-free palladium-based alloys.

The typical composition of such alloys can be found in the "Survey of Dental Noble-Metal Alloys and Dental Base Metal Alloys in the Federal Republic of Germany" [in German] published by the Research Institute for Dental Care (FZV), Vol 1., (July 1986), pp. 31–2. In addition to palladium and silver, these alloys contain primarily tin, indium and zinc, in individual instances also copper or gallium as further alloying elements.

The disadvantage of these alloys is the fact that they discolor the dental ceramic to a yellow or a yellowish green during the firing process. This discoloration is caused by the silver, which passes by diffusion or via the vapor phase into the ceramics.

DE-PS 25 23 971 describes palladium-silver alloys which contain 0.1 to 0.5 % titanium in order to suppress the discoloration of the ceramics. As a result of the reactivity of titanium with the atmospheric oxygen and/or the crucible materials, the melt becomes impoverished of this element relatively rapidly so that the reducing action on the tendency toward discoloration is lost when using old material (runners, casting funnels) and under unfavorably selected melting conditions. Moreover, the titanium brings about a strong adhesion of the investment material to the surface of the cast object, which makes it more difficult and more time-consuming to divest and to finish it.

U.S. Pat. No. 4,350,526 describes palladium-silver alloys which exhibit no discoloring action on dental ceramics due to the addition of 0.1–1.0% silicon. Silicon is insoluble both in palladium and in silver. Moreover, palladium and silicon form intermetallic phases, so that a strong embrittlement of the alloy and fracture after casting can occur.

Silicon favors, similar to titanium, a reaction with ceramic materials, so that a strong adhesion of the material to the cast object also occurs in the case of these alloys.

SUMMARY OF THE INVENTION

An object of the present invention is to provide palladium-silver alloys for the manufacture of fixed or removable dentures which can be veneered with dental ceramics and onto which alloys discoloration-sensitive dental ceramics can be burned without recognizable changes in color and which can be easily removed from the customary inestment material without the other properties of the known palladium-silver alloys significantly changing.

In achieving the above and other objects, one feature of the invention resides in using palladium-silver alloys consisting of 45 to 80% by weight palladium, 7 to 50% by weight silver, 0 to 5% by weight gold, 0 to 2% by weight platinum, 0 to 5% by weight tin, 0 to 5% by weight indium, 0 to 3% by weight zinc, 0 to 2% by weight copper, 0 to 1% by weight tungsten, molybdenum and/or tantalum, 0 to 1% by weight ruthenium, iridium and/or rhenium, 0 to 7% by weight gallium, 0 to 5% by weight cobalt and 0 to 3% by weight germanium and further, wherein at least two of the elements gallium, cobalt and germanium must be present in the alloys with contents totalling 2 to 9% by weight.

It is preferable to use alloys which contain 55 to 75% palladium and 20 to 45% by weight silver in addition to the other components. Moreover, it has proven to be advantageous if 0.5 to 4% by weight gallium, 1 to 4% by weight cobalt and 0.1 to 1.5% by weight germanium are present in the alloys, whereby the sum of these contents must be between 2 and 7% by weight.

Especially advantageous alloys contain 60 to 68% by weight palladium, 28 to 32% by weight silver, 0.1 to 0.5% by weight ruthenium, iridium and/or rhenium, 1.5 to 2.5% by weight gallium, 1.5 to 2.5% by weight cobalt and 1 to 1.5% by weight germanium.

Palladium-silver alloys become corrosion resistant the mouth above a palladium content of approximately 25–30%. Alloys with a silver content of more than 50% by weight exhibit very high coefficients of thermal expansion (>16.0× $10^{-6}$/K), so that they are no longer compatible with conventional veneering ceramics. If the silver contents are too low, the palladium-silver alloys behave similarly to silver-free palladium-based alloys. For this reason, palladium-silver alloys in a range of 45–80% palladium and 7–50% silver were selected, which exhibit an excellent corrosion resistance in the mouth and offer the prerequisite for a crack-free veneering of the alloy with dental ceramics.

The elements tin, indium, zinc, copper and gold serve to set the mechanical properties of the alloys, such as for example strength, hardness, melting and casting properties, coefficient of thermal expansion and melting range Ruthenium, rhenium and/or iridium are alloyed therewith in concentrations between 0.1 and 1% as grain refinement additives.

However, palladium-silver alloys which contain only the previously mentioned alloying elements discolor the dental ceramics distinctly yellowish-green during the firing process.

It was surprisingly found that the addition of gallium, cobalt and geranium in the concentration ranges in accordance with the invention distinctly reduces or eliminates the discoloring action of the alloys designated above on the dental ceramics. This reduction or elimination of the tendency to discolor is only observed, however, if at least two of these three elements are present in the alloy. If the sum of the contents of at least two of the three elements gallium, germanium and cobalt is less than 2%, the discoloring action on the ceramics is still relatively strong. If this sum exceeds 9%, the other properties of the alloy are negatively influenced, so that a concentration range between 2 and 9% must be maintained.

Table 1 shows the composition and the properties of a few alloys in accordance with the invention. They have excellent melting and casting properties bright oxide and can be veneered without difficulties with the known dental ceramics. The high yield strength paired with a high elongation permits these alloys to also be used for removable partial dentures The determination of the color of the dental ceramics on the alloys after being fired on was performed with a color-measuring device (datacolor—Light Colour Systems GmbH, light type D 65, angle of observation 10°) and visually by several persons in comparison to a "standard specimen". A gold-reduced, silver-free alloy of the composition 52.0% by weight gold, 37.6% by weight palladium, 8% by weight indium, 2.0% by weight gallium and 0.4% by weight iridium was used as standard alloy and the brightest color of a commercial veneer ceramics assortment was used as ceramics.

Table 2 summarizes the results of the color measurement of known reference alloys and of a few alloys in accordance with the invention according to table 1 (color values according to the CIELab-System, DIN 6174). The L value indicates the position on the bright-dark axis (L=0) black, L=100 white ) The "a" value describes the position on the green/red axis (negative=green, positive red) and the "b" value the position on the blue/yellow axis (blue negative, yellow positive).

Table 2 does not show the absolute color values but rather the deviation of the color values for the ceramic veneer on the different alloys from the standard specimen (Δ values). The color values of the alloys in accordance with the invention are in the range of the known, silver-free alloys or alloys with a high gold content. Even a visual observation of veneered crowns and bridges was not able to detect any deviation in color of the alloys in accordance with the invention from the standard specimen.

Further variations and modifications of the foregoing will be apparent to those skilled in the art and are intended to be encompassed by the claims appended hereto.

German priority application P 38 06 343.3 is relied on and incorporated herein.

TABLE 1

| Alloying No. | Composition in % by weight | | | | | | | | | | | Melting interval [°C.] | Hardness after ceramic firing cycle HV5 | Coeffic. of th. exp. RT 600° C. $[10^{-6}K^{-1}]$ | (MPa) | elongation [%] |
|---|---|---|---|---|---|---|---|---|---|---|---|---|---|---|---|---|
| | Au | Pd | Ag | Ru | Sn | In | Cu | Zn | Ga | Ge | Co | W | | | | |
| 1 | — | 64.5 | 30 | 0.5 | — | — | — | — | 3 | 1 | — | | 1291–1150 | 200 | 15.15 | n.b. | n.b. |
| 2 | — | 63.3 | 30 | 0.5 | 2 | — | — | — | 2 | — | 2 | 02 | 1291–1192 | 220 | 14.9 | n.b. | n.b. |
| 3 | 2 | 60.5 | 30 | 0.5 | 4 | — | — | — | — | 1 | 2 | | 1307–1213 | 210 | n.b. | n.b. | n.b. |
| 4 | — | 64 | 30 | 0.5 | — | 2 | — | — | 2 | 1.5 | — | | 1287–1140 | 205 | 15.0 | n.b. | n.b. |
| 5 | — | 64 | 30 | 0.5 | — | — | 1.5 | 1.0 | 2 | 1 | — | | 1296–1185 | 210 | 15.0 | n.b. | n.b. |
| 6 | — | 63.5 | 30 | 0.5 | 2 | — | — | — | 2 | 1 | 1 | | 1270–1170 | 210 | 15.0 | 559 | 23.6 |
| 7 | — | 65.1 | 30 | 0.5 | — | — | — | — | 1 | 1.4 | 2 | | 1298–1192 | 230 | n.b. | 552 | 25.7 |
| 8 | — | 62.5 | 30 | 0.5 | 10 | 10 | — | — | 2 | 1 | 2 | | 1249–1155 | 210 | 15.3 | n.b. | n.b. |
| 9 | — | 62.5 | 30 | 0.5 | — | 1 | — | — | 2 | 1 | 3 | | 1245–1148 | 240 | 14.9 | n.b. | n.b. |
| 10 | — | 77.5 | 10 0 | 0.5 | 4 | — | — | — | 4 | — | 4 | | 1301–1204 | 190 | n.b. | n.b. | n.b. |
| 11 | — | 55.5 | 40 | 0.2 | 1 | — | — | — | 2 | 1 | — | | 1266–1175 | 180 | 15.8 | n.b. | n.b. |

TABLE 2

| Alloy | ΔL | Δa | Δb |
|---|---|---|---|
| 1 Au 52 Pd 37 6 In 8 Ga 2 0 Ir 0 4 (Standard) | 0 | 0 | 0 |
| 2 1 (according to Table 1) | 0 | 0 | 0.5 |
| 3 2 (according to Table 1) | −0.5 | 0.3 | 0.4 |
| 4 4 (according to Table 1) | −2.9 | 0.1 | 0.8 |
| 5 6 (according to Table 1) | −0.6 | 0.2 | 0.5 |
| 6 7 (according to Table 1) | −1.9 | 0.2 | −0.1 |
| 7 Au 77.3 Pd 8.9 Pt 9 8 | −1.6 | 0.2 | 0.2 |
| 8 Au 53.2 Pd 35.1 Sn 6.6 Co 2.8 | −1.4 | 0.5 | 0.3 |
| 9 Pd 79 Ga 9 Cu 9 5 | 0.9 | 0.3 | 1.0 |
| 10 Pd 79.7 Sn 6.5 Ga6 Cu 5 | −3.1 | 0.1 | −0.7 |
| 11 Pd 76.5 Cu 11.6 Ga 7.2 | −1.7 | 0.5 | 0.3 |
| 12 Pd 57.8 Ag 30 Sn 6 In 4 | 0.7 | 0.2 | 3.1 |
| (In reference alloys 7 to 12, only those components are indicated which are over 2% by weight.) | | | |

We claim:

1. A fixed or removable partial denture which can be veneered with dental ceramics, which denture is formed from a palladium-silver alloy comprising 45 to 80% by weight palladium, 7 to 50% by weight silver, 0 to 5% by weight gold, 0 to 2% by weight platinum, 0 to 5% by weight tin, 0 to 5% by weight indium, 0 to 3% by weight zinc, 0 to 2% by weight copper, 0 to 1% by weight tungsten, molybdenum and/or tantalum, 0 to 1% by weight ruthenium, iridium and/or rhenium, 0 to 7% by weight gallium, 0 to 5% by weight cobalt and 0.1 to 3% by weight germanium, wherein at least two of the elements gallium, cobalt and germanium must be present in the alloys with a content totalling 2 to 9% by weight.

2. The denture according to claim 1, wherein the alloy has a content of 55 to 75% by weight palladium and 20 to 45% by weight silver.

3. The denture according to claim 1, wherein the alloy has a content of 0.5 to 4% by weight gallium, 1 to 4% by weight cobalt and 0.1 to 1.5% by weight germanium and wherein the sum of these components must be between 2 and 7% by weight.

4. The denture according to claim 1, wherein the alloy is 60 to 68% by weight palladium, 28 to 32% by weight silver, 0.1 to 0.5% by weight ruthenium, iridium and/or rhenium, 1.5 to 2.5% by weight gallium, 1.5 to 2.5% by weight cobalt and 1 to 1.5% by weight germanium.

5. The denture according to claim 1 which has a ceramic adhered thereto.

* * * * *